United States Patent [19]
Nakagawa et al.

[11] 3,994,901
[45] Nov. 30, 1976

[54] 5-[1-HYDROXY-2-(SUBSTITUTED-AMINO)]ALKYL-8-HYDROXY-3,4-DIHYDROCARBOSTYRIL DERIVATIVES

[75] Inventors: Kazuyuki Nakagawa, Tokushima; Shiro Yoshizaki, Naruto; Kaoru Tanimura; Shigeharu Tamada, both of Tokushima, all of Japan

[73] Assignee: Otsuka Pharmaceutical Company Limited, Tokyo, Japan

[22] Filed: Dec. 26, 1974

[21] Appl. No.: 536,516

[30] Foreign Application Priority Data

| June 13, 1974 | Japan | 49-67824 |
| Nov. 11, 1974 | Japan | 49-130721 |
| Nov. 11, 1974 | Japan | 49-130722 |
| Nov. 11, 1974 | Japan | 49-130723 |
| Nov. 11, 1974 | Japan | 49-130724 |
| Nov. 11, 1974 | Japan | 49-130725 |
| Nov. 11, 1974 | Japan | 49-130728 |
| Dec. 4, 1974 | Japan | 49-140339 |
| Dec. 4, 1974 | Japan | 49-140340 |

[52] U.S. Cl. ............ 260/288 R; 260/288 CE; 260/289 K; 424/250
[51] Int. Cl.² ............ C07D 215/22; C07D 215/26
[58] Field of Search ...... 260/288 R, 288 CE, 289 K

[56] References Cited
UNITED STATES PATENTS
3,444,173  5/1969  Goldman .................. 260/288 R OTHER PUBLICATIONS
Morrison et al.; Organic Chemistry (1969), pp. 666, 866, 567.
Chodnekar et al.; *J. Med. Chem.* vol. 15, pp. 49–57 (1972).

*Primary Examiner*—Nicholas S. Rizzo
*Assistant Examiner*—Mary C. Vaughn
*Attorney, Agent, or Firm*—Sughrue, Rothwell, Mion, Zinn & Macpeak

[57] ABSTRACT

5-[1-Hydroxy-2-(substituted-amino)]alkyl-8-hydroxy-3,4-dihydrocarbostyril derivatives having the formula (I)

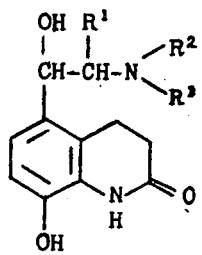

(I)

wherein $R^1$ represents an alkyl group having 1 to 4 carbon atoms, and $R^2$ and $R^3$, which may be the same or different, each represents a hydrogen atom, an alkyl group having 1 to 4 carbon atoms, an aralkyl group containing a straight or branched chain alkyl moiety having 1 to 4 carbon atoms or a cycloalkyl group having 4 to 6 carbon atoms, or $R^2$ and $R^3$ may, when taken together with the nitrogen atom to which they are attached, form a 5- or 6-membered substituted or unsubstituted heterocyclic ring containing 1 or 2 nitrogen, oxygen or sulfur atoms as hetero atoms, the pharmaceutically acceptable acid addition salts thereof, and a process for preparing the same. These compounds posess a β-adreno-receptor stimulating activity.

11 Claims, No Drawings

5-[1-HYDROXY-2-(SUBSTITUTED-AMINO)]ALKYL-8-HYDROXY-3,4-DIHYDROCARBOSTYRIL DERIVATIVES

BACKGROUND OF THE INVENTION

1. FIELD OF THE INVENTION

This invention relates to novel carbostyril derivatives and a process for preparing the same. More particularly, this invention relates to novel 5-[1-hydroxy-2-(substituted-amino)]-alkyl-8-hydroxy-3,4-dihydrocarbostyril derivatives, the pharmaceutically acceptable acid addition salts thereof, and a process for preparing the same.

2. DESCRIPTION OF THE PRIOR ART

It is well known that certain carbostyril derivatives exhibit useful pharmaceutical activities. Representative compounds of this type have been disclosed in *Journal of Medical Chemistry*, Vol. 15, No. 3, pp. 260 – 266 (1972), Japanese Patent Publication No. 38789/1971 and *Chemical Abstracts*, 62, 16212e (1965), etc. However, these prior art references do not teach that the compounds having a 1-hydroxy-2-(substituted-amino)alkyl group at the 5-position of the carbostyril moiety possess an excellent β-adreno-receptor stimulating activity.

It has now been found that 8-hydroxy-3,4-dihydrocarbo-styril derivatives having a 1-hydroxy-(2-substituted-amino)alkyl group at the 5-position of the carbostyril moiety and the pharmaceutically acceptable acid addition salts thereof possess a β-adreno-receptor stimulating activity, and therefore, are useful as a therapeutic agent such as a bronchodilator, a peripheral vasodilator and an antihypertensive agent, particularly for treating bronchial asthma.

SUMMARY OF THE INVENTION

This invention provides novel 5-[1-hydroxy-2-(substituted-amino)]alkyl-8-hydroxy-3,4-dihydrocarbostyril derivatives having the formula (I)

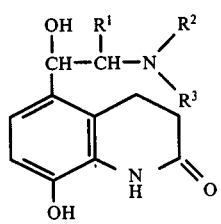

wherein $R^1$ represents an alkyl group having 1 to 4 carbon atoms, and $R^2$ and $R^3$, which may be the same or different, each represents a hydrogen atom, an alkyl group having 1 to 4 carbon atoms, an aralkyl group containing a straight or branched chain alkyl moiety having 1 to 4 carbon atoms or a cycloalkyl group having 4 to 6 carbon atoms, or $R^2$ and $R^3$ may, when taken together with the nitrogen atom to which they are attached, form a 5- or 6-membered substituted or unsubstituted heterocyclic ring containing 1 or 2 nitrogen, oxygen or sulfur atoms as hetero atoms.

This invention also provides a process for preparing the above 5-[1-hydroxy-2-(substituted-amino)]alkyl-8-hydroxy-3,4-dihydrocarbostyril derivatives represented by the formula (I)

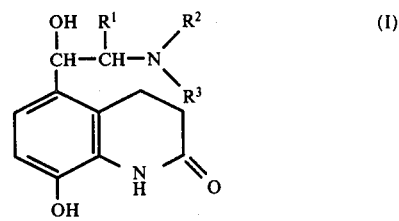

wherein $R^1$ represents an alkyl group having 1 to 4 carbon atoms, and $R^2$ and $R^3$, which may be the same or different, each represents a hydrogen atom, an alkyl group having 1 to 4 carbon atoms, an aralkyl group containing a straight or branched chain alkyl moiety having 1 to 4 carbon atoms or a cycloalkyl group having 4 to 6 carbon atoms, or $R^2$ and $R^3$ may, when taken together with the nitrogen atom to which they are attached, form a 5- or 6-membered substituted or unsubstituted heterocyclic ring containing 1 or 2 nitrogen, oxygen or sulfur atoms as hetero atoms, and the pharmaceutically acceptable acid addition salts thereof which comprises the steps of:

1. reacting a 8-substituted-3,4-dihydrocarbostyril of the formula (VI)

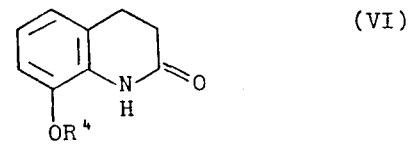

wherein $R^4$ represents a hydrogen atom or an alkyl group having 1 to 4 carbon atoms, with an α-haloalkanoic acid of the formula (V)

wherein $R^1$ is as defined above and X and X', which may be the same or different, each represents a halogen atom, in the presence or absence of a solvent and in the presence of a Lewis acid catalyst, to produce the corresponding 5-(α-haloalkanoyl)-8-substituted-3,4-dihydrocarbostyril of the formula (IV)

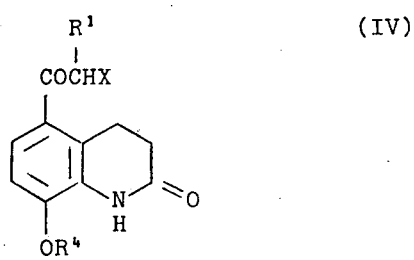

wherein $R^1$, $R^4$ and X are as defined above, 2. reacting the resulting 5-(α-haloalkanoyl)-8-substituted-3,4-dihydrocarbostyril of the formula (IV) with an amine of the formula (III)

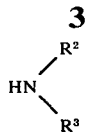
(III)

wherein R² and R³ are as defined above, to produce a 5-(α-substituted-aminoalkanoyl)-8-alkoxy-3,4-dihydrocarbostyril of the formula (IIa)

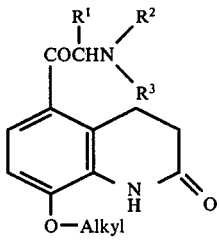
(IIa)

wherein "alkyl" represents an alkyl group having 1 to 4 carbon atoms and R¹, R², and R³ are as defined above, or a 5-(α-substituted-aminoalkanoyl)-8-hydroxy-3,4-dihydrocarbostyril of the formula (IIb)

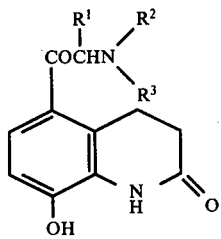
(IIb)

wherein R¹, R², and R³ are as defined above, and dealkylating the carbostyril of the formula (IIa) with a hydrogen halide to produce the 5-(α-substituted-aminoalkanoyl)-8-hydroxy-3,4-dihydrocarbostyril of the formula (IIb), and 3. reducing the resulting 5-(α-substituted-aminoalkanoyl)-8-hydroxy-3,4-dihydrocarbostyril with hydrogen in the presence of a hydrogenation catalyst or with a reducing agent.

The 5-[1-hydroxy-2-(substituted-amino)]alkyl-8-hydroxy-3,4-dihydrocarbostyril derivatives of the formula (I) and the acid addition salts thereof are novel compounds and exhibit a β-adreno-receptor stimulating activity and, therefore, are useful as a bronchodilator, a peripheral vasodilator or an antihypertensive agent, particularly for treating bronchial asthma.

DETAILED DESCRIPTION OF THE INVENTION

The term "alkyl" as used herein means a straight or branched chain alkyl group having 1 to 4 carbon atoms, and includes, for example, a methyl, ethyl, propyl, isopropyl, butyl, sec-butyl, tert-butyl group and the like.

The term "aralkyl" as used herein means an aralkyl group containing a straight or branched chain alkyl moiety having 1 to 4 carbon atoms, for example, a benzyl, α-methylbenzyl, α,α-dimethylbenzyl, phenethyl, α,α-dimethylphenethyl group and the like.

The term "cycloalkyl" as used herein means a cycloalkyl group having 4 to 6 carbon atoms, for example, a cyclobutyl, cyclopentyl, cyclohexyl group and the like.

The term "5- or 6-membered substituted or unsubstituted heterocyclic ring" used herein means heterocyclic groups containing 1 or 2 nitrogen, oxygen or sulfur atoms as hetero atoms such as a pyrrolidino, pyrrolidinyl, piperidino, piperidinyl, morpholino, morpholinyl, piperazino, piperazinyl or a like group which can be unsubstituted or substituted with an alkyl group having 1 to 4 carbon atoms, such as a methyl, ethyl, isopropyl, tert-butyl group and the like, for example, a 2-methylpiperidino, 3-methylpiperidino, N-methylpiperazino group and the like.

The compounds of the present invention represented by the formula (I) can be prepared from 8-hydroxy-3,4-dihydrocarbostyril according to the following reaction scheme:

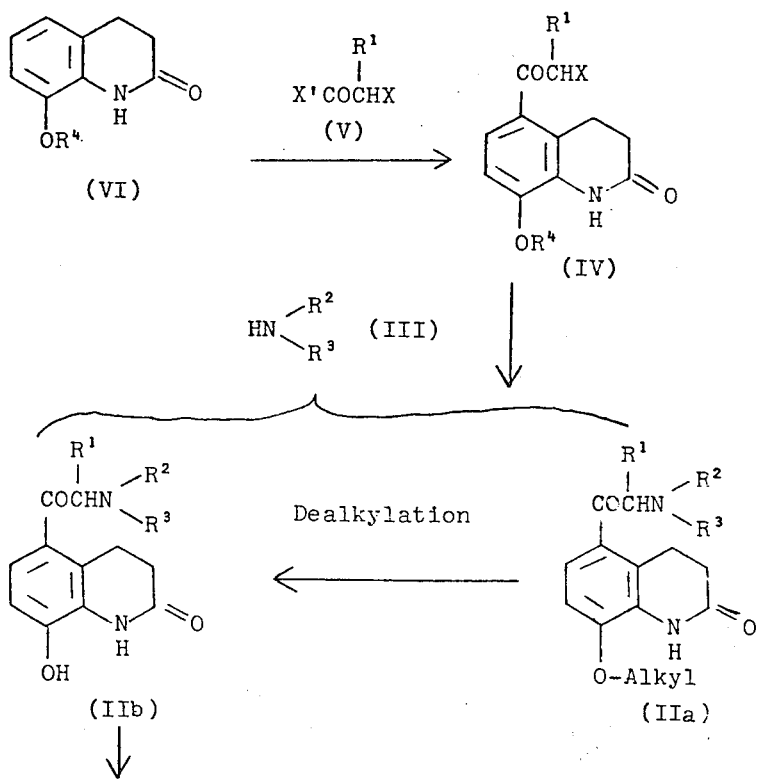

-continued

[H]↓

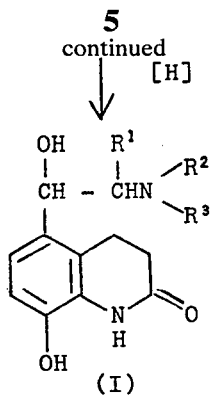
(I)

wherein R¹ represents an alkyl group having 1 to 4 carbon atoms; R² and R³, which may be the same or different, each represents a hydrogen atom, an alkyl group having 1 to 4 carbon atoms, an aralkyl group containing a straight or branched chain alkyl moiety having 1 to 4 carbon atoms or a cycloalkyl group having 4 to 6 carbon atoms, or R² and R³ may, when taken together with the nitrogen atom to which they are attached, form a 5- or 6-membered substituted or unsubstituted heterocyclic ring containing 1 or 2 nitrogen, oxygen or sulfur atoms as hetero atoms; R⁴ represents a hydrogen atom or an alkyl group having 1 to 4 carbon atoms; and X and X', which may be the same or different, each represents a halogen atom.

The 8-substituted-3,4-dihydrocarbostyril of the formula (VI) used as a starting material in the preparation of the compounds of the formula (IV) is a known compound and can easily be prepared by, for example, the method as disclosed in J. D. Loudon and J. Ogg; *J. Chem. Soc.*, 1955, 739 or Fritz Mayer, L. van Zutphen and H. Philips, *Ber.*, 60, 858 (1927).

As illustrated in the above reaction scheme, the 5-(α-haloalkanoyl)-8-substituted-3,4-dihydrocarbostyril represented by the formula (IV) which is an intermediate in the process of this invention can be prepared by reacting the corresponding 8-substituted-3,4-dihydrocarbostyril of the formula (VI) with an α-haloalkanoic acid halide of the formula (V)

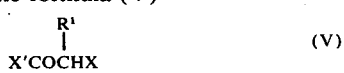

wherein R¹, X and X' are as defined above, in the presence of a Lewis acid.

The thus obtained 5-(α-haloalkanoyl)-8-alkoxy-3,4-dihydrocarbostyril (R⁴ =alkyl) or 5-(α-haloalkanoyl)-8-hydroxy-3,4-dihydrocarbostyril (R⁴ = H) of the formula (IV) is then reacted with a secondary or tertiary organic amine represented by the formula (III)

wherein R² and R³ are as defined above, in the presence or absence of a solvent to obtain a 5-(α-substituted-aminoalkanoyl)-8-substituted-3,4-dihydrocarbostyril derivative represented by the formula (II)

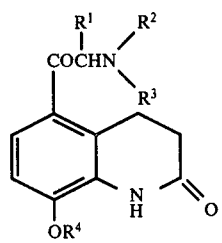
(II)

wherein R¹, R², R³, and R⁴ are as defined above, i.e., when R⁴ is an alkyl group, the corresponding 5-(α-substituted-aminoalkanoyl)-8-alkoxy-3,4-dihydrocarbostyril derivative represented by the formula (IIa)

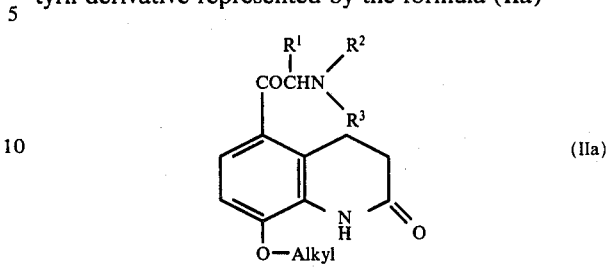

wherein "alkyl" represents an alkyl group having 1 to 4 carbon atoms as defined for R⁴ and R¹, R², and R³ are as defined above, or when R⁴ is a hydrogen atom, a 5-(α-substituted-aminoalkanoyl)-8-hydroxy-3,4-dihydrocarbostyril represented by the formula (IIb)

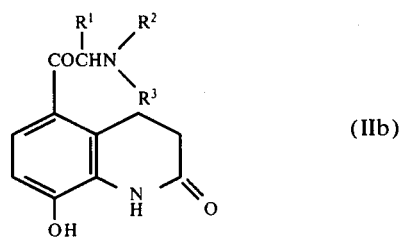

wherein R¹, R², and R³ are as defined above, respectively.

The 8-alkoxy compound of the formula (IIa) as obtained above can then be dealkylated with a hydrogen halide such as hydrogen bromide to form the corresponding 8-hydroxy compound of the formula (IIb).

The 5-[1-hydroxy-2-(substituted-amino)]alkyl-8-hydroxy-3,4-dihydrocarbostyril derivative of the formula (I) of the present invention can be prepared by reducing the above obtained 5-(α-substituted-aminoalkanoyl)-8-hydroxy-3,4-dihydrocarbostyril derivative of the formula (IIb).

Both of the compounds (IIb) and the compounds (I) of the present invention are novel compounds.

The process according to the present invention will be hereinafter illustrated in greater detail.

The α-haloalkanoic acid halide of the formula (V) which can be used in the present invention as a reactant in the preparation of the compound of the formula (IV) includes α-chloropropionyl chloride, α-bromopropionyl chloride, α-chlorobutyryl chloride, α-bromobutyryl chloride, α-bromobutyryl bromide, α-chlorovaleryl chloride and the like, preferably, α-chloropropyl chloride and α-chlorobutyl chloride. The reaction between the 3,4-dihydrocarbostyril of the formula (VI) and the α-haloalkanoic acid halide of the formula (V) is a so-called Friedel-Crafts reaction.

The catalyst which can be used in this reaction is a usual Lewis acid, for example, aluminum chloride or bromide, zinc chloride, ferric chloride, stannic chloride, titanium chloride, boron trifluoride and the like with aluminum chloride being preferably used. These catalysts are generally used in an amount of from 2 to 10 moles, preferably 3 to 6 moles, per mole of the compound of the formula (IV).

This reaction can be effected either in the absence of a solvent or in the presence of an inert organic solvent. Suitable examples of solvents which can be used in this reaction are carbon disulfide, nitrobenzene, diethyl ether, dioxane and the like, preferably, carbon disulfide. These solvents are usually used in a volume of about 0.5 to about 20, preferably 2 to 10, times the volume of the reactants.

This reaction is generally conducted using an equimolar amount to a large excess of the α-haloalkanoic acid halide of the formula (V) of about 2 to about 20 moles, preferably 2 to 10 moles, of the α-haloalkanoic acid halide of the formula (IV) per mole of the 8-substituted-3,4-dihydrocarbostyril of the formula (VI). The reaction proceeds at room temperature (about 20° to 30° C) to about 150° C, preferably room temperature to 80° C. The reaction time varies depending upon the reaction temperature employed, but is usually from about 1 to 20, preferably 1 to 10 hours. The reaction can preferably be carried out under anhydrous conditions.

The amine of the formula (III) which can be used as a reactant in the preparation of the 5-(α-substituted-aminoalkanoyl)-8-substituted-3,4-dihydrocarbostyrils of the formulae (IIa) and (IIb) includes alkylamines, for example, methylamine, ethylamine, n-propylamine, isopropylamine, n-butylamine, sec-butylamine, tert-butylamine and the like; cycloalkylamines, for example, cyclobutylamine, cyclopentylamine, cyclohexylamine; aralkylamines, for example, benzylamine, α-methylbenzylamine, α,α-dimethylbenzylamine, phenethylamine, α,α-dimethylphenethylamine and the like; and substituted or unsubstituted heterocyclic amines, for example, pyrrolidine, piperidine, morpholine, piperazine, 2-methylpiperidine, 3-methylpiperidine, N-methylpiperazine and the like.

The reaction between the 5-(α-haloalkanoyl)-8-substituted-3,4-dihydro-carbostyril intermediate of the formula (IV) and the amine of the formula (III) can be carried out either in the absence of a solvent because the amine of the formula (III) per se serves as a reaction solvent, or in the presence of an appropriate solvent. Suitable examples of solvents which can be used in this reaction include lower alcohols such as methanol, ethanol, isopropanol and the like, ethers such as dioxane, diethyl ether and the like, esters such as ethyl acetate, aromatic hydrocarbons such as benzene, toluene, xylene and the like, nitrile solvents such as acetonitrile and the like. Ethanol and isopropanol are preferably used.

This reaction can be effected using an equimolar amount to a large excess of the amine of the formula (III), preferably from about 2 to about 10 moles of the amine of the formula (III) per mole of the 5-(α-haloalkanoyl)-8-hydroxy-3,4-dihydrocarbostyril of the formula (IV) at room temperature to the refluxing temperature of the reaction system, preferably 40° to 100° C at atmospheric pressure to 10 atmospheres. When the reaction is effected without using any solvent, it is preferable to use a large excess of the amine of the formula (III) with respect to the carbostyril derivative of the formula (IV).

Thus, when the 8-hydroxy-3,4-dihydrocarbostyril of the formula (VI) wherein $R^4$ is a hydrogen atom is used as a starting material, the 5-(α-substituted-aminoalkanoyl)-8-hydroxy-3,4-dihydrocarbostyril of the formula (IIb) is obtained, which can be subjected to the subsequent reduction reaction to produce the 5-[1-hydroxy-2-(substituted-amino)]alkyl-8-hydroxy-3,4-dihydroxycarbostyril of the formula (I). When the 8-alkoxy-3,4-dihydrocarbostyril of the formula (VI) wherein $R^4$ is an alkyl group is used as a starting material, the corresponding 5-(α-substituted-aminoalkanoyl)-8-alkoxy-3,4-dihydrocarbostyril of the formula (IIa) is obtained. The resulting 5-(α-substituted-aminoalkanoyl)-8-alkoxy-3,4-dihydrocarbostyril of the formula (IIa) is then reacted with a hydrogen halide to dealkylate the 8-position of the 3,4-dihydrocarbostyril moiety thereby obtaining the compound of the formula (IIa), which can be subjected to the subsequent reduction reaction as indicated above.

The hydrogen halides used in this dealkylation include, for example, hydrogen bromide, hydrogen chloride, hydrogen iodide and the like, preferably, hydrogen bromide. These hydrogen halides can advantageously be employed in an appropriate solvent such as methanol, ethanol, propanols, preferably water, in a form of an aqueous solution of the hydrogen halide at a concentration of about 10 to 50%, preferably 47% hydrogen bromide.

This dealkylation reaction can generally be carried out using the hydrogen halide in an equimolar amount to, preferably, a large excess with respect to the compound of the formula (IIa) by heating at a temperature of from about 100° to about 150° C, preferably at reflux, for about 1 to about 20 hours, preferably 3 to 10 hours.

The reduction of the above obtained 5-substituted-aminoalkanoyl-8-hydroxy-3,4-dihydrocarbostyril derivative of the formula (IIb) to the 5-[1-hydroxy-2-(substituted-amino)]alkyl-8-hydroxy-3,4-dihydrocarbostyril derivative of the formula (I) can be conducted by a conventional reduction using a reducing agent such as lithium aluminum hydride, sodium borohydride and the like, or a conventional catalytic reduction with hydrogen in the presence of a hydrogenation catalyst such as palladium black, palladium-on-carbon, Raney nickel, platinum black, platinum oxide and the like.

The above reducing agent can be used in an amount of from about 2 to about 10 moles, preferably 2 to 5 moles, per mole of the carbostyril compound of the formula (IIb) in a solvent while cooling under atmospheric pressure at a temperature of from about 0° to about 100° C, preferably 20° to 50° C. When sodium borohydride is used as the reducing agent, the solvent is preferably water or an alcohol such as methanol, ethanol and the like, and when lithium aluminum hydride is used as the reducing agent, the solvent is preferably a non-aqueous solvent such as anhydrous diethyl ether, ethyl acetate, tetrahydrofuran and the like.

The catalytic reduction can be carried out with hydrogen using the above hydrogenation catalyst in an amount of from about 0.05 to about 1 mole, preferably 0.1 to 0.5 mole, per mole of the carbostyril compound of the formula (IIb) in a solvent, for example, water or an alcohol such as methanol, ethanol or isopropanol under a hydrogen atmosphere at a pressure of from about atmospheric pressure to about 100 atmospheres, preferably atmospheric pressure to 50 atmospheres, at a temperature of from room temperature to about 150° C, preferably room temperature to 120° C, advantageously with agitating the reduction system. It is advantageous to carry out the above catalytic reduction at a temperature higher than about 50° C at atmospheric pressure or at a temperature higher than room temperature under pressure.

Alternatively, the compound of the formula (I) of the present invention can also be prepared by catalytically reducing the corresponding 5-(α-substituted-aminoalkanoyl)-8-hydroxycarbostyril derivative having the formula (VII)

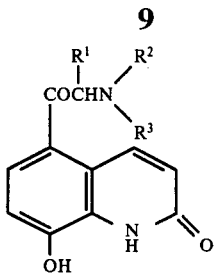

(VII)

wherein $R^1$, $R^2$, and $R^3$ are as defined above.

The 5-(α-substituted-aminoalkanoyl)-8-hydroxycarbostyril derivative of the formula (VII) which can be used as a reactant in the above described reduction and a process for preparing the same are disclosed and claimed in co-pending application U.S. patent application Ser. No. 536515, filed Nov. 26, 1974, filed simultaneously herewith.

The catalytic reduction initially results in the production of a 5-(1-hydroxy-2-substituted-aminoalkyl)-8-hydroxycarbostyril of the formula (VIII)

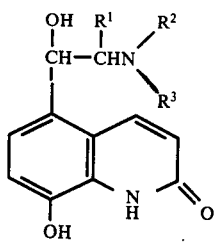

(VIII)

wherein $R^1$, $R^2$, and $R^3$ are as defined above or the 5-(α-substituted-aminoalkanoyl)-8-hydroxy-3,4-dihydrocarbostyril having the formula (IIb) as described hereinbefore, which is then subjected to further reduction to form the compound of the formula (I).

The reduction of the 5-(α-substituted-aminoalkanoyl)-8-hydroxycarbostyril derivative of the formula (VII) to the compound of the formula (I) can be carried out in a solvent such as water, methanol, ethanol, isopropanol, ethyl acetate and the like in the presence of a catalyst, e.g., palladium black, platinum oxide, palladium-on-carbon, platinum black, Raney nickel and the like at room temperature to about 150° C, preferably room temperature to 120° C in a hydrogen atmosphere of about 1 to about 100, preferably 1 to 50, atmospheres.

The compound of the formula (I) can also be prepared by dealkylating the corresponding 5-[1-hydroxy-2-(substituted-amino)]alkyl-8-alkoxy-3,4-dihydrocarbostyril derivative represented by the formula (IX)

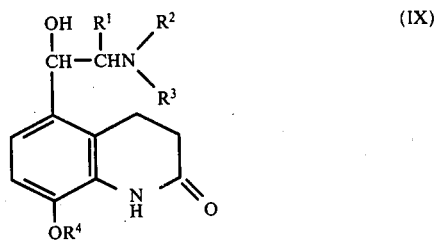

(IX)

wherein $R^1$, $R^2$, $R^3$, and $R^4$ are as defined above with a hydrogen halide.

The 5-[1-hydroxy-2-(substituted-amino)]alkyl-3,4-dihydrocarbostyril derivatives of the formula (IX) above and the process for preparing the same are disclosed in co-pending U.S. patent application Ser. No. 536703, filed Dec. 26, 1974.

This dealkylation can be carried out under the same reaction conditions as used in this invention with respect to the dealkylation of the compound (IIa).

Both the compounds of the formula (IIa) and the compounds of the formula (I) as obtained above are basic substances and can form acid addition salts with various organic or inorganic acids. Particularly useful such salts are the pharmaceutically acceptable acid addition salts formed with inorganic acids such as hydrochloric acid, sulfuric acid, phosphoric acid, hydrobromic acid, etc., or organic acids such as oxalic acid, maleic acid, fumaric acid, malic acid, tataric acid, citric acid, ascorbic acid, etc. These acid addition salts can easily be prepared by well-known procedures, for example, by adding an equimolar to an excess amount of the acid to a solution of the compound dissolved in an appropriate organic solvent such as methanol, ethanol, isopropanol, acetone and the like.

Both the free bases of the compounds (I) and the acid addition salts thereof exhibit a stimulating activity on β-adreno-receptor and, therefore, are very useful as pharmaceuticals for treating disorders such as bronchial asthma. As is apparent to one skilled in the art, the compounds of the present invention contain two asymmetrical centers and, therefore, can be present in four optically active forms. Particularly preferred compounds of the formula (I) are the following basic compounds and their hydrochlorides, sulfates, phosphates, maleates, fumarates and oxalates.

5-(1-Hydroxy-2-isopropylamino)propyl-8-hydroxy-3,4-dihydrocarbostyril 5-(1-Hydroxy-2-isopropylamino)butyl-8-hydroxy-3,4-dihydrocarbostyril 5-(1-Hydroxy-2-tert-butylamino)butyl-8-hydroxy-3,4-dihydrocarbostyril 5-(1-Hydroxy-2-sec-butylamino)butyl-8-hydroxy-3,4-dihydrocarbostyril 5-(1-Hydroxy-2-tert-butylamino)propyl-8-hydroxy-3,4-dihydrocarbostyril 5-(1-Hydroxy-2-isopropylamino)ethyl-8-hydroxy-3,4-dihydrocarbostyril 5-(1-Hydroxy-2-amino)ethyl-8-hydroxy-3,4-dihydrocarbostyril 5-(1-Hydroxy-2-ethylamino)butyl-8-hydroxy-3,4-dihydrocarbostryril The present invention is further illustrated by reference to the following Examples, but these examples are given for the purposes of illustration and not to be construed as limiting the scope of the invention. Unless otherwise indicated, all parts, percents, ratios and the like are by weight.

EXAMPLE 1

17.1 g of α-bromopropionyl chloride (V), 27 g of anhydrous aluminum chloride and 8 ml of nitrobenzene were added to 8 g of 8-methoxy-3,4-dihydrocarbostyril (VI), and the mixture was heated at a temperature of 50° to 60° C for 1 hour while stirring. The reaction mixture was then poured into 200 ml of ice-water, and the precipitate formed was filtered and washed with water. The precipitate was then recrystallized from ethanol to obtain 11.5 g of a material having a melting point of 154° – 155° C. The product thus obtained was confirmed by NMR and IR spectral analyses and elemental analysis to be 5-(α-bromopropionyl)-8-methoxy-3,4-dihydrocarbostyril (IV).

EXAMPLE 2

26.4 g of α-bromobutyryl bromide (V), 17.5 g of anhydrous aluminum chloride and 5 ml of nitrobenzene were added to 5 g of 8-methoxy-3,4-dihydrocarbostyril (VI), and the mixture was heated at a temperature of 50° to 60° C for 1 hour while stirring. The reaction mixture was then poured into 100 ml of ice-water, and the precipitate formed was filtered and washed with water. The precipitate was then recrystallized from ethanol to obtain 5 g of a material having a melting point of 151° – 152° C. The product thus obtained was confirmed by NMR and IR spectral analyses and elemental analysis to be 5-(α-bromobutyryl)-8-methoxy-3,4-dihydrocarbostyril (IV).

EXAMPLE 3

2 g of the 5-(α-bromopropionyl)-8-methoxy-3,4-dihydrocarbostyril (IV) prepared as described in Example 1 was suspended in 50 ml of isopropanol, and the suspension was stirred for 2 hours at a temperature of 60° C. The solvent was then distilled off, and the resulting residue was dissolved in 5 ml of isopropanol. The solution was then adjusted to a pH of 2 – 3 with concentrated hydrochloric acid. The precipitate formed was filtered and a mixture of acetone and diethyl ether was added to the filtrate. The precipitate formed was filtered and recrystallized from isopropanol to obtain 1.5 g of a white amorphous material having a melting point of 172° – 174° C (with decomposition). The product thus obtained was confirmed by NMR and IR spectral analyses and elemental analysis to be 5-(α-isopropylaminopropionyl)-8-methoxy-3,4-dihydrocarbostyril (IIa) hydrochloride dihydrate.

EXAMPLE 4

5 g of 5-(α-bromopropionyl)-8-methoxy-3,4-dihydrocarbostyril (IV) prepared as described in Example 1 was suspended in 50 ml of isopropanol, and 10 g of t-butylamine (III) was added to the suspension followed by stirring the mixture at a temperature of 60° C for 15 hours. The solvent was then distilled off, and the resulting residue was dissolved in 10 ml of isopropanol. The solution was then adjusted to a pH of 2 – 3 with concentrated hydrochloric acid. The precipitate formed was filtered and acetone was added to the filtrate. The precipitate formed was filtered, and diethyl ether was added to the filtrate. The precipitate formed was filtered and recrystallized from a mixture of isopropanol and diethyl ether to obtain 2.1 g of a colorless amorphous material having a melting point of 207° – 210° C (with decomposition). The product thus obtained was confirmed by NMR and IR spectral analyses and elemental analysis to be 5-(α-t-butylaminopropionyl)-8-methoxy-3,4-dihydrocarbostyril (IIa) hydrochloride monohydrate.

EXAMPLE 5

2 g of 5-(α-bromobutyryl)-8-methoxy-3,4-dihydrocarbostyril (IV) prepared as described in Example 2 was suspended in 50 ml of isopropanol, and 5 g of isopropylamine (III) was added to the suspension followed by stirring the mixture at a temperature of 60° C for 4 hours. The solvent was then distilled off, and the resulting residue was dissolved in 5 ml of isopropanol. The solution was then adjusted to a pH of 2 – 3 with concentrated hydrochloric acid. The precipitate formed was filtered and recrystallized from a mixture of isopropanol and acetone to obtain 1.7 g of a colorless amorphous material having a melting point of 204° – 206° C (with decomposition). The product thus obtained was confirmed by NMR and IR spectral analyses and elemental analysis to be 5-(α-isopropylaminobutyryl)-8-methoxy-3,4-dihydrocarbostyril (IIa) hydrochloride monohydrate.

EXAMPLE 6

3 g of 5-(α-bromobutyryl)-8-methoxy-3,4-dihydrocarbostyril (IV) prepared as described in Example 2 was suspended in 50 ml of isopropanol, and 9 g of t-butylamine (III) was added to the suspension followed by stirring the mixture at a temperature of 60° C for 19 hours. The solvent was then distilled off, and the resulting residue was dissolved in 5 ml of isopropanol. The solution was then adjusted to a pH of 2 – 3 with concentrated hydrochloric acid. The precipitate formed was filtered, and acetone was added to the filtrate. The precipitate formed was filtered and diethyl ether was added to the filtrate. The precipitate formed was filtered and recrystallized from isopropanol to obtain 1.6 g of a colorless amorphous material having a melting point of 160° – 162° C (with decomposition). The product thus obtained was confirmed by NMR and IR spectral analyses and elemental analysis to be 5-(α-t-butylaminobutyryl)-8-methoxy-3,4-dihydrocarbostyril (IIa) hydrochloride monohydrate.

EXAMPLE 7

1.5 g of 5-(α-isopropylaminopropionyl)-8-methoxy-3,4-dihydrocarbostyril (IIa) prepared as described in Example 4 was dissolved in 15 ml of a 47% aqueous hydrobromic acid and the solution was refluxed for 15 hours under heating at a temperature of 140° C. The reaction mixture was concentrated, and acetone was added to the reaction mixture to crystallize the product. The product was then recrystallized from a mixture of ethanol and acetone to obtain 1.1 g of a material having a melting point of 223° – 226° C (with decomposition). The product thus obtained was confirmed by NMR and IR spectral analyses and elemental analysis to be 5-(α-isopropylaminopropionyl)-8-hydroxy-3,4-dihydrocarbostyril (IIb) hydrobromide.

EXAMPLE 8

1.5 g of 5-(α-isopropylaminobutyryl)-8-methoxy-3,4-dihydrocarbostyril (IIa) was dissolved in 15 ml of a 47% aqueous hydrobromic acid and the solution was refluxed for 15 hours under heating at a temperature of 130° – 140° C. The reaction mixture was concentrated, and acetone was added to the reaction mixture to crystallize the product. The product was then recrystallized from a mixture of ethanol and acetone to obtain 1.0 g of a material having a melting point of 165° – 168° C. The product thus obtained was confirmed by NMR and IR spectral analyses and elemental analysis to be 5-(α-isopropylaminobutyryl)-8-hydroxy-3,4-dihydrocarbostyril (IIb) hydrobromide ½ hydrate.

EXAMPLE 9

1 g of 5-(α-t-butylaminopropionyl)-8-methoxy-3,4-dihydrocarbostyril (IIa) obtained from the hydrochloride monohydrate prepared as described in Example 4 was dissolved in 15 ml of a 47% aqueous hydrobromic acid and the solution was refluxed for 15 hours under heating at a temperature of 140° to 150° C. The reaction mixture was concentrated, and acetone was added to the reaction mixture to crystallize the product. The product was then recrystallized from a mixture of ethanol and acetone to obtain 0.7 g of a material having a melting point of 224° – 227° C (with decomposition). The product thus obtained was confirmed by NMR and IR spectral analyses and elemental analysis to be 5-(α-t-butylaminopropionyl)-8-hydroxy-3,4-dihydrocarbostyril hydrobromide (IIb) monohydrate.

EXAMPLE 10

1.5 g of 5-(α-t-butylaminobutyryl)-8-methoxy-3,4-dihydrocarbostyril (IIa) obtained from the hydrochloride monohydrate prepared as described in Example 6 was dissolved in a 47% aqueous hydrobromic acid and the solution was refluxed for 19 hours at a temperature of 140° to 150° C. The reaction mixture was concentrated, and acetone was added to the reaction mixture to crystallize the product. The product was then recrystallized from a mixture of ethanol and acetone to obtain 1.1 g of a material having a melting point of 114° – 146° C (with decomposition). The product thus obtained was confirmed by NMR and IR spectral analyses and elemental analysis to be 5-(α-t-butylaminobutyryl)-8-hydroxy-3,4-dihydrocarbostyril (IIb) hydrobromide dihydrate.

EXAMPLE 11

5 g of 5-(α-bromopropionyl)-8-hydroxy-3,4-dihydrocarbostyril (IV) was suspended in 30 ml of benzene, and 4.2 ml of morpholine (III) was added to the suspension followed by allowing the mixture to react for 4 hours while heating under refluxing. The reaction mixture was filtered and the filtrate was washed with water followed by concentration under reduced pressure to remove any remaining water. The resulting residue was dissolved in 50 ml of isopropanol, and the solution was adjusted to a pH of 2 – 3 with concentrated hydrochloric acid. The viscous precipitate formed upon ice-cooling was separated and dissolved in acetone by heating. After allowing the solution to cool, the precipitate formed was dissolved in 30 ml of water and adjusted to a pH of 7.5 – 8 with sodium bicarbonate. The precipitate formed upon ice-cooling was filtered and dissolved in 10 ml of a 47% aqueous hydrobromic acid followed by concentration under reduced pressure. The residue thus obtained was washed with 10 ml of ethanol and recrystallized from ethanol to obtain 2.6 g of white amorphous 5-(α-morpholinopropionyl)-8-hydroxy-3,4-dihydrocarbostyril (IIb) hydrobromide monohydrate having a melting point of 235° – 236° C (with decomposition).

EXAMPLE 12

1.0 g of 5-(α-isopropylaminopropionyl)-8-hydroxy-3,4-dihydrocarbostyril (IIb) obtained from the hydrobromide ½ hydrate prepared as described in Example 8 was dissolved in 50 ml of methanol, and 0.3 g of sodium borohydride was added slowly to the solution while ice-cooling followed by stirring the mixture at room temperature for 1 hour. Methanol which had been saturated with hydrogen chloride gas was then added to the mixture to adjust the mixture to a pH of 1 – 2. The precipitate formed was filtered, and the filtrate was concentrated to dryness. A 1N aqueous sodium hydroxide solution was then added to the residue to a pH of 7.5 – 8, and the precipitate formed was filtered, dissolved in ethanol and hydrogen chloride gas was bubbled into the solution. The precipitate formed was filtered and recrystallized from ethanol to obtain 0.8 g of a material having a melting point of 211° – 213° C. The product thus obtained was confirmed by NMR and IR spectral analyses and elemental analysis to be 5-(1-hydroxy-2-isopropylamino)propyl-8-hydroxy-3,4-dihydrocarbostyril (I) hydrochloride ½ hydrate.

EXAMPLE 13

To 1.0 g of 5-(α-isopropylaminobutyryl)-8-hydroxy-3,4-dihydrocarbostyril (IIb) were added 20 ml of ethanol and 0.05 g of platinum oxide, and the mixture was reduced under a hydrogen pressure of 2 atmospheres at a temperature of 60° C for 10 hours. After completion of the reduction, the catalyst was removed by filtration, and the filtrate was adjusted to a pH of 1 with concentrated hydrochloric acid and concentrated to dryness. The resulting residue was recrystallized from ethanol to obtain 0.9 g of a material having a melting point of 196° – 198° C. The product thus obtained was confirmed by NMR and IR spectral analyses and elemental analysis to be 5-(1-hydroxy-2-isopropyl(amino)butyl-8-hydroxy-3,4-dihydrocarbostyril (I) hydrochloride monohydrate.

EXAMPLE 14

To 1.0 g of 5-(α-tert-butylaminopropionyl)-8-hydroxy-3,4-dihydrocarbostyril (IIb) hydrobromide obtained from the corresponding monohydrate prepared in Example 9 were added 50 ml of water and 0.2 g of palladium black, and the mixture was reduced under atmospheric pressure at a temperature of 60° C for 20 hours. After completion of the reduction, the catalyst was filtered and the filtrate was concentrated to dryness. The resulting residue was recrystallized from ethanol to obtain 0.75 g of a material having a melting point of 198° – 199° C (with decomposition). The product thus obtained was confirmed by NMR and IR spectral analyses and elemental analysis to be 5-(1-hydroxy-2-tert-butylamino)propyl-8-hydroxy-3,4-dihydrocarbostyril (I) hydrobromide monohydrate.

EXAMPLE 15

To 1.0 g of 5-(α-tert-butylaminobutyryl)-8-hydroxy-3,4-dihydrocarbostyril hydrobromide (IIb) obtained from the corresponding dihydrate prepared in Example 10 were added 50 ml of water and 0.2 g of palladium black, and the mixture was reduced under atmospheric pressure at a temperature of 80° C for 10 days. After completion of the reduction, the catalyst was filtered, and the filtrate was concentrated to dryness. The resulting residue was recrystallized from ethanol to obtain 0.7 g of a material having a melting point of 164° – 166° C (with decomposition). The product thus obtained was confirmed by NMR and IR spectral analyses and elemental analysis to be 5-(1-hydroxy-2-tert-butylamino) butyl-8-hydroxy-3,4-dihydrocarbostyril (I) hydrobromide (as an ethanol solvate).

EXAMPLE 16

To 2 g of 5-(α-isopropylaminobutyryl)-8-hydroxycarbostyril (VII) were added 0.1 g of palladium black and 50 ml of ethanol, and the mixture was reduced at a hydrogen pressure of 35 atmospheres at a temperature of 75° C for 15 hours while shaking the mixture. After completion of the reduction, the catalyst was filtered, and the filtrate was adjusted to a pH of 1 with concentrated hydrochloric acid. The mixture was then concentrated to dryness and the resulting precipitate was recrystallized from ethanol to obtain 1.7 g of 5-(1-hydroxy-2-isopropylamino) butyl-8-hydroxy-3,4-dihydrocarbostyril (I) hydrochloride monohydrate having a melting point of 196° – 198° C.

EXAMPLE 17

To 1 g of 5-(α-isopropylaminobutyryl)-8-hydroxycarbostyril hydrochloride (VII) were added 0.05 g of platinum black and 100 ml of water, and the mixture was reduced at a hydrogen pressure of 40 atmospheres at a temperature of 60° C for 18 hours with shaking the mixture. After completion of the reduction, the catalyst was filtered, and the filtrate was concentrated to dryness. The precipitate formed was then recrystallized from isopropanol to obtain 0.85 g of 5-(1-hydroxy-2-isopropylamino)-butyl-8-hydroxy-3,4-dihydrocarbostyril (I) hydrochloride monohydrate having a melting point of 196° – 198° C.

EXAMPLE 18

To 0.5 g of 5-(α-sec-butylaminobutyryl)-8-hydroxycarbostyril (VII) were added 0.0025 g of palladium black and 15 ml of ethanol, and the mixture was reduced at a hydrogen pressure of 50 atmospheres at a temperature of 80° C for 15 hours while shaking the mixture. After completion of the reduction, the catalyst was filtered, and the filtrate was adjusted to a pH of 1 with concentrated hydrochloric acid and concentrated to dryness. The precipitate formed was then recrystallized from ethanol to obtain 0.45 g of 5-(1-hydroxy-2-sec-butylamino)-butyl-8-hydroxy-3,4-dihydrocarbostyril hydrochloride monohydrate having a melting point of 205° – 207° C.

EXAMPLE 19

15 ml of a 47% aqueous hydrobromic acid was added to 1.5 g of 5-(1-hydroxy-2-tert-butylamino)propyl-8-methoxy-3,4-dihydrocarbostyril (IX), and the mixture was heated under refluxing for a period of 15 hours. Thereafter, acetone was added to the reaction mixture to crystallize the product, and the resulting crystals were recrystallized from a mixture of ethanol and acetone to obtain 1.4 g of a material having a melting point of 198° – 199° C (with decomposition). The product thus obtained was confirmed by NMR and IR spectral analyses and elemental analysis to be 5-(1-hydroxy-2-tert-butylamino)propyl-8-hydroxy-3,4-dihydrocarbostyril (I) hydrobromide monohydrate.

In the same manner as described in Example 19, the following compounds of the formula (I) were prepared from the corresponding 8-methoxy compounds of the formula (IX).

5-[1-Hydroxy-2-(2-phenethylamino)]butyl-8-hydroxy-3,4-dihydrocarbostyril hydrochloride having a melting point of 127° – 129° C (with decomposition)

5-(1-Hydroxy-2-morpholino)butyl -8-hydroxy-3,4-dihydrocarbostyril hydrobromide having a melting point of 183° – 185° C (with decomposition)

5-(1-Hydroxy-2-ethylamino)butyl -8-hydroxy-3,4-dihydrocarbostyril hydrochloride having a melting point of 213° – 214.5° C (with decomposition).

EXAMPLE 20

To 1.0 g of 5-(α-tert-butylaminobutyryl)-8-hydroxy-3,4-dihydrocarbostyril hydrobromide (IIb) were added 50 ml of water and 0.2 g of palladium black, and the mixture was reduced at atmospheric pressure at a temperature of 80° C for 10 days. After completion of the reduction, the catalyst was filtered, and the filtrate was concentrated to dryness. The resulting residue was recrystallized from ethanol to obtain 0.7 g of a material having a melting point of 164° – 166° C (with decomposition). The product thus obtained was confirmed by NMR and IR spectral analyses and elemental analysis to be 5-(1-hydroxy-2-tert-butylamino)butyl-8-hydroxy-3,4-dihydrocarbostyril (I) hydrobromide (as an ethanol solvate).

EXAMPLE 21

1.0 g of 5-(2-morpholinobutyryl)-8-hydroxy-3,4-dihydrocarbostyril (IIb) hydrobromide was dissolved in 70 ml of water and 0.2 g of palladium-on-carbon and 0.3 g of palladium black were added to the solution followed by allowing the mixture to catalytically reduce under atmospheric pressure in a hydrogen atmosphere for 10 days at a temperature of 70° C while shaking. After completion of the reduction, the reaction mixture was filtered to remove the catalysts by filtration, and the filtrate was concentrated to dryness under reduced pressure. The resulting residue was dissolved in acetone by heating followed by allowing the solution to cool. The precipitate formed upon cooling was recrystallized from ethanol to obtain 0.7 g of white amorphous 5-(2-morpholino-1-hydroxybutyl)-8-hydroxy-3,4-dihydrocarbostyril (I) hydrobromide 1/2 hydrate having a melting point of 183° – 185° C (with decomposition). The product thus obtained was confirmed by NMR and IR spectral analyses and elemental analysis.

REFERENCE EXAMPLE

The stimulating activity of the compounds of this invention on β-adreno-receptor was determined as follows:

Male hybrid adult dogs, weighing 10 to 15 kg were anesthesized with 30 mg/kg of body weight of sodium pentobarbital administered intravenously. Each of the anesthesized dogs were secured on its back and a cannula was inserted into the trachea. Artificial respiration was conducted using a device according to the Konzett-Rössler method (Konzett H. & Rössler R., "Versuchsanordnug zu Untersuchungen an der Bronchial Moskolatur", *Arch. Exp. Path., Pharmack*, 195, 71 – 74, 27 – 40 (1940)). The volume of the overflowing air at the time of inhalation was measured through a pneumotachometer to determine the bronchial resistance and the values obtained were recorded on a polygraph.

In the above experiment, histamine was employed as a bronchoconstrictor at a dosage level of 10 mg/kg of body weight, and an aqueous solution containing each of the test compounds and controls shown in Table 1 below was then administered to each of the anesthesized dogs through the femoral vein at various dosage levels shown in Table 1 below 1 minute before the administration of the histamine. Sodium pentobarbital was infused during the experiment at a dosage level of 4 mg/kg of body weight/hr using an automatic injector in order to inhibit spontaneous respiration and to keep the anesthetic condition constant over the test period. The results obtained are shown in Table 1 below.

Table 1

| | Bronchial Resistance (%) | | | | | | | | |
|---|---|---|---|---|---|---|---|---|---|
| | Dosage Level (ug/Kg) | | | | | | | | |
| Compound | 0.01 | 0.03 | 0.1 | 0.3 | 1.0 | 3.0 | 10 | 30 | 100 |
| 5-(1-Hydroxy-2-isopropylamino)-butyl-8-hydroxy-carbostyril Hydrochloride | 0 | 13.5 | 33.7 | 73.2 | 92.3 | 100 | — | — | — |
| 5-(1-Hydroxy-2-tert-butylamino)-propyl-8-hydroxy-carbostyril Hydrochloride | 0 | 5.7 | 21.4 | 65.0 | 81.8 | 100 | — | — | — |
| (Control) | | | | | | | | | |
| Isoproterenol | 0 | 16.6 | 58.3 | 83.3 | 100 | — | — | — | — |
| Salbutamol | 0 | 0 | 16.6 | 33.3 | 66.6 | 100 | — | — | — |
| Metaproterenol Sulfate (Arotec) | 0 | 0 | 2.7 | 11.1 | 27.5 | 50.0 | 88.3 | 100 | — |
| Quinterenol | 0 | 0 | 0 | 0 | 0 | 0 | 0 | 7.6 | 15.3 |

Further, the acute toxicity was determined with respect to a representative compound of the present invention, 5-(1-hydroxy-2-isopropylamino)butyl-8-hydroxy-3,4-dihydrocarbostyril, using 5 to 6 groups each containing 10 male rats (dd strain; body weight, 18 to 22 g) which had been fasted for 12 hours prior to the test. Salbutamol and isoproterenol were used as a control. The $LD_{50}$ (50% lethal dose) results are as follows.

Table 2

| | $LD_{50}$ (mg/Kg) | |
|---|---|---|
| Compound | I.v. | p.o. |
| 5-(1-Hydroxy-2-isopropylamino)-butyl-8-hydroxy-3,4-dihydro-carbostyril Hydrochloride | 81.5 (72.4–91.8) | 830 (542–1270) |
| (Control) Salbutamol | 57.1 (52.7–61.9) | 4620* (4160–5130) 660 (412.5–1056) |
| Isoproterenol | 112.5 (87.9–144.0) | 2587* 355 (235.1–536.1) |

Note:
*Literature values

The compounds of the present invention can be administered at a dosage level of from 100δ to 50 mg/Kg/day by oral, intravenous, intrarectal or inhalation administration in a conventional pharmaceutical dosage form such as a tablet, powder, granule, capsule, syrup, solution, suspension, inhalant (aerosol spray), suppository and the like, preferably, in combination with pharmaceutically acceptable carriers or diluents which are well known in the art.

Pharmaceutical compositions generally comprise at least one compound of the present invention and pharmaceutical carriers or diluents which are commonly employed in conventional pharmaceutical compositions. The composition may contain other active components which do not adversely affect the activities of the compounds of this invention.

Suitable pharmaceutical carriers or diluents include solid carriers such as corn starch, calcium sulfate dihydrate, magnesium stearate, lactose, Aerosil (trademark of Nihon Aerosil Co., Ltd., Japan) and the like which are suitable for use in oral, suppository, injectable and inhalant formulations. The oral dosage forms can be formulated in accordance with well known procedures and conveniently formulated into tablets which can be optionally provided with a sugar coating. A soluble tablet which is suitable for sublingual administration, i.e., troche or lozenge, can also be prepared.

The injectable composition can be prepared using physiologically acceptable carriers or diluents in the form of a solution, suspension or dry preparation which is reconstituted instantaneously with a vehicle for injection just before administration.

The compounds of the present invention are advantageously administered in the form of an aerosol spray formulation by inhalation.

Typical examples of suitable formulations are given below, but it is to be noted that other dosage forms can also be prepared using other compounds of this invention according to the well-established techniques.

Formulation 1

Tablets each containing the following components were prepared from the following components:

| Component | Amount |
|---|---|
| 5-(1-Hydroxy-2-isopropylamino)butyl-8-hydroxy-3,4-dihydrocarbostyril | 1 mg |
| Corn Starch | 70 mg |
| Magnesium Stearate | 9 mg |
| Lactose | 20 mg |
| Total | 100 mg |

Formulation 2

Aerosol spray for inhalation containing the following components per each dose was prepared and filled in the aerosol dispenser:

| Component | Amount |
|---|---|
| 5-(1-Hydroxy-2-isopropylamino)butyl-8-hydroxy-3,4-dihydrocarbostyril | 50 mcg |
| Oleic Acid | 10 mcg |
| Dichlorodifluoromethane | 57 mg |
| Trichlorofluoromethane | 25 mg |

While the present invention has been described in detail with reference to specific embodiments thereof, it is apparent to one skilled in the art that various changes and modifications can be made therein without departing from the spirit and the scope of the present invention.

What is claimed is:

1. A 5-[1-hydroxy-2-(substituted-amino)]alkyl-8-hydroxy-3,4-dihydrocarbostyril compound having the formula

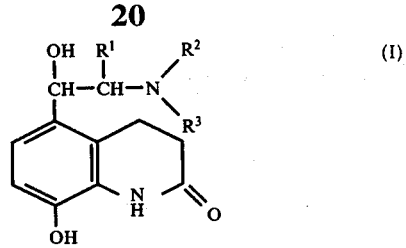

wherein $R^1$ represents an alkyl group having 1 to 4 carbon atoms, and $R^2$ and $R^3$, which may be the same or different, each represents a hydrogen atom, an alkyl group having 1 to 4 carbon atoms, a phenylalkyl group wherein the alkyl moiety is straight or branched chain alkyl having 1 to 4 carbon atoms or cycloalkyl having 4 to 6 carbon atoms, or $R^2$ and $R^3$ may, when taken together with the nitrogen atom to which they are attached, form a 5- or 6-membered substituted, by an alkyl group having 1 to 4 carbon atoms, or unsubstituted heterocyclic ring selected from the group consisting of pyrrolidino and piperidino, and the pharmaceutically acceptable acid addition salts thereof.

2. 5-(1-Hydroxy-2-isopropylamino)propyl-8-hydroxy-3,4-dihydrocarbostyril according to claim 1.

3. 5-(1-Hydroxy-2-isopropylamino)butyl-8-hydroxy-3,4-dihydrocarbostyril according to claim 1.

4. 5-(1-Hydroxy-2-tert-butylamino)butyl-8-hydroxy-3,4-dihydrocarbostyril according to claim 1.

5. 5-(1-Hydroxy-2-sec-butylamino)butyl-8-hydroxy-3,4-dihydrocarbostyril according to claim 1.

6. 5-(1-Hydroxy-2-tert-butylamino)propyl-8-hydroxy-3,4-dihydrocarbostyril according to claim 1.

7. 5-(1-Hydroxy-2-isopropylamino)ethyl-8-hydroxy-3,4-dihydrocarbostyril according to claim 1.

8. 5-(1-Hydroxy-2-amino)ethyl-8-hydroxy-3,4-dihydrocarbostyril according to claim 1.

9. 5-(1-Hydroxy-2-ethylamino)butyl-8-hydroxy-3,4-dihydrocarbostyril according to claim 1.

10. 5-[1-Hydroxy-2-(2-phenethylamino)butyl]-8-hydroxy-3,4-dihydrocarbostyril according to claim 1.

11. 5-(1-Hydroxy-2-tert-butylamino)propyl-8-hydroxy-3,4-dihydrocarbostyril according to claim 1.

* * * * *